US006407290B2

(12) United States Patent
Herwig et al.

(10) Patent No.: US 6,407,290 B2
(45) Date of Patent: Jun. 18, 2002

(54) PROCESS FOR THE PRODUCTION OF SUBSTITUTED 10-CHLORO-PHENOXAPHOSPHINES OR 10-BROMO-PHENOXAPHOSPHINES

(75) Inventors: Jurgen Herwig, Hunxe; Peter Skutta, Oberhausen; Stefanie Sturm, Dinslaken, all of (DE)

(73) Assignee: Celanese Chemicals Europe GmbH (DE)

( * ) Notice: Subject to any disclaimer, the term of this patent is extended or adjusted under 35 U.S.C. 154(b) by 0 days.

(21) Appl. No.: 09/845,962

(22) Filed: Apr. 30, 2001

(30) Foreign Application Priority Data

May 6, 2000 (DE) .......................................... 100 22 186

(51) Int. Cl.⁷ ................................................. C07F 9/50
(52) U.S. Cl. ....................................................... 568/12
(58) Field of Search ........................................... 568/12

(56) References Cited

U.S. PATENT DOCUMENTS 4,698,447 A * 10/1987 Blum ........................... 568/12

OTHER PUBLICATIONS

CA:130:252068 abs of Angew chem INt Ed by Van der Veen et al 38(3) pp 336–338.*
J Am. Chem. Soc. vol. 110 by Vedejs pp 3948–3958 1988.*
J Organic Chemistry vol. 31 No 1 by Levy et al Jan. 1968.*
XP–001013580, Chem. Ber. 111 pp. 13–41 (1978).
XP–000964505 Organometallics 1999, 18, 4765–4777.

* cited by examiner

*Primary Examiner*—Jean F. Vollano
(74) *Attorney, Agent, or Firm*—Bierman, Muserlian and Lucas

(57) ABSTRACT

An efficient process for the production of substituted 10-chloro-phenoxaphosphines or 10 bromo-phenoxaphosphines by reaction of substituted diphenyl ethers with phosphorus trihalogenide in the presence of at least one Lewis acid and subsequent treatment with an amine.

18 Claims, No Drawings

PROCESS FOR THE PRODUCTION OF SUBSTITUTED 10-CHLORO-PHENOXAPHOSPHINES OR 10-BROMO-PHENOXAPHOSPHINES

STATE OF THE ART 10-chloro-phenoxaphosphine and 10-bromo-phenoxaphosphine are important intermediates in the synthesis of metallo-organic complexing ligands as well as in the synthesis of phenoxaphosphinic acids. Complexing ligands form an essential component of the catalyst system in homogenous catalysis. Phenoxaphosphine derivatives are used as subunits for complexing ligands in a multiplicity of catalytic reactions, such as hydroformylations, hydrogenations, hydroxycarbonylations, alkoxycarbonylation or allylic alkylations, wherein, to some extent, extremely high selectivities can be attained with simultaneous high conversions and turn-over frequencies of the catalyst system. Thus, Hobbs et al describes in J. Org. Chem., Vol. 46, 4424 (1981), the asymmetric rhodium-catalyzed hydroformylation of vinyl acetate using a DIOP derivative as a ligand which contains two phenoxaphosphine subunits.

From the literature, processes are already known for the production of 10-chloro-phenoxaphosphines. Freedman et al describes in J. Organ. Chem. 1961, Vol 26, 284 the conversion of p-tolyl ether with phosphorus trichloride and aluminum trichloride. After the aqueous processing, the reaction product was identified as 2,8-dimethyl-phenoxaphosphinic acid. The 2,8-dimethyl-phenoxaphosphinc acid can be converted analogously to the teaching of Hellwinkel and Krapp in Chem. Ber. 1978, Vol 111, 13 for dibenzophosphoric acid by reaction with phosphorus oxychloride at 200° C. and subsequent reaction with red phosphorus at 180° C. to form 10-chloro-2,8-dimethylphenoxaphosphine. The synthesis from ether is thus a three-stage synthesis and the total yield is 59.6% over all stages. Thus, an economical production of the compound is not possible.

OBJECTS OF THE INVENTION

It is an object of the invention to provide an economical process to prepare substituted 10-chloro-phenoxaphosphines or the corresponding substituted 10-bromo-phenoxaphosphines in high yield and purity in a technically simple manner.

This and other objects and advantages of the invention will become obvious from the following detailed description.

THE INVENTION

The process of the invention for the preparation of substituted 10-chloro-phenoxaphosphines and 10-bromo-phenoxaphosphines comprises reacting a substituted diphenyl ether with a phosphorus trihalide in the presence of at least one Lewis acid and reacting the resulting product with an amine to produce the substituted 10-halo-phenoxaphosphine.

It has surprisingly been found that the addition of amines for a multiplicity of substituted 10-chloro-phenoxaphosphines and 10-bromo-phenoxaphosphines, which will be referred to in the following as 10-halogen-phenoxaphosphines, permits carrying out the reaction in a single stage under mild conditions with low yield losses. Through the addition of amines, the intermediately formed complex of substituted 10-chloro-phenoxaphosphine and metal chloride or of substituted 10-bromo-phenoxaphosphine and metal bromide can be cleaved under conditions in the absence of water, whereby the hydrolysis of the substituted 10-halogen-phenoxaphosphines (halogen= Cl, Br) to the free acid is prevented. The conversion is illustrated in the following scheme.

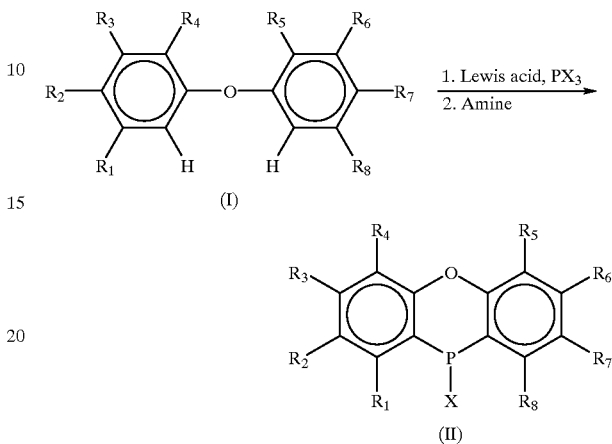

The substituents of the 10-halogen-phenoxaphosphines of formula (II) and the diphenyl ether (I) used as the starting compound can be varied over a wide range. Thus, $R_1$, $R_3$, $R_4$, $R_5$, $R_6$ and $R_8$ are independently selected from the group consisting of hydrogen, alkyl and alkoxy of 1 to 22 carbon atoms, acyloxy of 1 to 22 carbon atoms, alkylthio of 1 to 22 carbon atoms, dithioacyloxy of 1 to 22 carbon atoms, aryloxy of 6 to 18 carbon atoms, arylthio of 6 to 18 carbon atoms, phenyl, fluorine, chlorine, bromine, iodine, $-NO_2$, $CF_3SO_3-$, $-CN$, $HCO-$, $RSO_2-$, $RSO-$, dialkylamino of 1 to 8 alkyl carbon atoms, AlK—NHCO—, AlKCO—, AlK'COO—, HCO—NH—, benzoyl, benzoyloxy, AlK'COO—CH=CH—, $Ar_2PO-$, AlK is alkyl of 1 to 4 carbon atoms, AlK' is alkyl of 1 to 8 carbon atoms, Ar is phenyl unsubstituted or substituted with at least one alkyl of 1 to 4 carbon atoms, $R_2$ and $R_7$ are individually selected from the group consisting of alkyl and alkoxy of 1 to 22 carbon atoms, alkylthio of 1 to 22 carbon atoms, dithioacyloxy of 1 to 22 carbon atoms, aryloxy of 6 to 18 carbon atoms, arylthio of 6 to 18 carbon atoms, phenyl, fluorine, chlorine, bromine, iodine, $-NO_2$, $CF_3SO_3-$, $-CN$, HCO—, $RSO_2-$, RSO—, dialkylamino of 1 to 8 alkyl carbon atoms, AlK—NH—CO—, AlKCO—, AlK'COO—, HCO—NH—, benzoyl, benzoyloxy, AlK'COO—CH=CH and $Ar_2PO-$. X is chlorine or bromine.

Preferably, $R_1$, $R_3$, $R_4$, $R_5$, $R_6$ and $R_8$ are individually selected from the group consisting of hydrogen, alkyl and alkoxy of 1 to 22 carbon atoms, acyloxy of 1 to 22 carbon atoms, aryloxy of 6 to 18 carbon atoms, phenyl, fluorine, chlorine, bromine, $-NO_2$, $-CN$ and $CF_3SO_3-$. $R_2$ and $R_7$ are preferably individually selected from the group consisting of alkyl and alkoxy of 1 to 22 carbon atoms, acyloxy of 1 to 22 carbon atoms, aryloxy of 6 to 18 carbon atoms, phenyl, fluorine, chlorine, bromine, $-NO_2$, $-CN$ and $CF_3SO_3-$.

More preferably, $R_1$, $R_3$, $R_4$, $R_5$, $R_6$ and $R_8$ are individually selected from the group consisting of hydrogen, alkyl of 1 to 22 carbon atoms, phenyl, fluorine, and chlorine. X is preferably chlorine.

Compounds in which $R_2$ and/or $R_7$ are hydrogen, are not suitable for this reaction, since, in this case, a bond linkage with the inclusion of the phosphorus atom, can also occur in the para position to the ether bridge. The products formed herein lead to phosphorus-bridged chains formed through intermolecular reaction instead of to substituted 10-chlorophenoxaphosphines which are formed by intramolecular cyclization.

The conversion of (I) with the phosphorus trihalide in the presence of at least one Lewis acid is carried out at a temperature of 0 to 200° C., preferably 0 to 150° C. and especially preferred at 50 to 120° C. While, according to the process, it is possible for the invention to use a phosphorus halide and a Lewis acid with different halogen substituents, this can lead to the formation of a mixture of bromo and chloro derivatives due to halogen exchange reactions.

The process of the invention is generally carried out at pressures of 0.1 to 2 MPa but it is preferred to conduct the reaction at atmospheric pressure. Conversions at increased pressure serve essentially for raising the boiling point of the optionally used solvent to be able to set the optimum reaction temperature.

To reach complete conversion, at least a stoichiometric equivalent of the phosphorus halide must be added to the substituted diphenyl ether. Markedly excess quantities are not detrimental. They are suitably distilled off, together with an optional solvent, after the completion of the reaction and before addition of the amine. Excess quantities of the phosphorus halide can serve as a further solubilizer or as complete replacement of an inert solvent.

Examples of Lewis acids are halides of main group III, as well as of subgroups VIII, I, and II of the periodic system of elements. Particularly preferred are zinc halides, copper halides, iron halides and aluminum halides. Especially preferred are zinc-II-chloride, copper-II-chloride, aluminum trichloride, aluminum tribromide, and iron-II-chloride. The Lewis acids can be used in the form of the pure salt as well as on substrate materials, such as silica gel.

To carry out the process of the invention, the Lewis acid is usually added to the diphenyl ether in a molar excess of up to the 1.5-fold. While greater excess quantities are possible, it is not useful for reasons of economy and ecology. Preferred is a molar excess of up to 1.2-fold of the Lewis acid and especially preferred is a maximally equimolar use of the Lewis acid relative to the diphenyl ether. However, it is also possible to use the Lewis acid in a lesser quantity than that stoichiometrically required.

It has surprisingly been found that already at a molar ratio of Lewis acid to diphenyl ether of 0.7: 1, yields of 80% of 10-halogen-phenoxaphosphine of formula (II) are obtained.

The reaction can be carried out with or without a solvent. Suitable solvents are aliphatic ethers and inert hydrocarbons. As examples of aliphatic ethers and inert hydrocarbons are toluene, tetrahydrofuran, diethyl ether, hexane, cyclohexane, pentane and benzene. The amount of solvent is selected so that the concentration of diarylethers is 0.1 to 80 percent by weight. The reaction is preferably carried out without solvents.

The complex of 10-halogen-phenoxaphosphine and the Lewis acid is cleaved by adding an amine after completion of the reaction. Preferred for this purpose are trialkylamine of 3 to 12 carbon atoms, a mixed tertiary alkylarylamine of 8 to 22 carbon atoms, an alicyclic amine of 4 to 8 carbon atoms with an optional oxygen as a further heteroatom, or a heterocyclic amine of 4 to 22 carbon atoms. Examples are trimethylamine, triethylamine, tri-n-butylamine, N,N-dimethylaniline, pyridine, α-picoline, morpholine, piperidine, and quinoline. Especially preferred amines for setting free the 10-halogen-phenoxaphosphine are triethylamine and pyridine.

The amines are in general added to the reaction mixture in amounts of 0.5 to 5 molar equivalents, preferably 0.9 to 3, and more preferably 1 to 2.5 molar equivalent, relative to the Lewis acid. Depending on their state of aggregation, the amines can be used in the form of the pure liquid or the pure solid.

Cleaving the complex of 10-halogen-phenoxaphosphine and Lewis acid is carried out at a temperature of −100 to 100° C., preferably at −100 to 50° C., more preferred at −50 to 25° C.

The 10-halogen-phenoxaphosphine is subsequently extracted with a solvent. After filtering off the separated Lewis acid-amine adduct and removing the solvent from the filtrate, the 10-halogen-phenoxaphosphine remains as a solid or an oil. Possible solvents which can be used are aliphatic ethers and inert hydrocarbons. Examples of aliphatic ethers and inert hydrocarbons are toluene, tetrahydrofuran, diethyl ether, hexane, cyclohexane, pentane and benzene.

In the following examples, there are described several preferred embodiments to illustrate the invention. However, it is to be understood that the invention is not intended to be limited to the specific embodiments.

EXAMPLE 1

59.4 g (0.3 mol) of p-tolylether [4,4'-dimethyl-diphenyl ether], 165 g (1.2 mol) of phosphorus trichloride and 51 g (0.38 mol) of anhydrous aluminum trichloride (added carefully) were heated for 8 hours at reflux. The excess phosphorus trichloride was then distilled off and 100 mol of toluene were added to the solid reside and toluene was distilled off again. The residue was suspended in 250 mol of toluene and 64 ml 0.79 mol of pyridine were slowly added dropwise at −10° C. with a light yellow precipitate forming. The precipitate of the Lewis acid-pyridine adduct was filtered off. After washing twice with 50 ml of toluene, the wash solution was combined with the yellow filtrate and dried in vacuo to obtain an 83% yield of a solid which was colored light yellow.

NMR-$^1$H (CDCl$_3$; ppm); δ=7.52 (d, 2H, J=7.3 Hz), 7.29 (d, 2H, J=7.4 Hz), 7.16 (d, 2H, J=5.7 Hz), 2.33 (s, 6H). NMR-$^{31}$P (CDCl$_3$; ppm): δ=37.7.

EXAMPLE 2

10.0 g (0.05 mol) of p-tolylether [4,4'-dimethyl-diphenyl ether], 39 g (0.28 mol) of phosphorus trichloride and 3.3 g (0.025 mol) of anhydrous aluminum trichloride were heated for 11 hours at reflux. The excess phosphorus trichloride was distilled off and 25 ml of toluene were added to the solid residue and toluene was distilled off again. The residue was suspended in 50 ml of toluene and 4 g of pyridine (0.05 mol) were slowly added dropwise at 0° C. with a whitish-yellow precipitate forming. The mixture was stirred for 4 hours and the precipitate of Lewis acid-pyridine adduct was filtered off. After washing twice with 10 mol of toluene, the wash solution was combined with the yellow filtrate and the solvent was evaporated in vacuo to obtain 10.6 g (80%) of the theoretical solid remained which was colored light yellow.

EXAMPLE 3

40.0 g (0.20 mol) of p-tolylether, 113.3 g (0.82 mol) of phosphorus trichloride and 40 g (0.30 mol) of anhydrous aluminum trichloride (added carefully) were heated for 8 hours at reflux. The excess phosphorus trichloride was distilled off and the solid residue was washed twice with 200 mol of toluene. The residue was suspended in 180 ml of toluene and 30.3 g (0.3 mol) of triethylamine were slowly added dropwise at −10° C. The precipitate of the Lewis acid-pyridine adduct was filtered off. After washing twice with 100 ml of toluene, the wash solution was combined with the yellow filtrate and dried in vacuo to obtain 34.4 g (65% yield) of a slightly yellow-colored solid.

Various modifications of the process of the invention may be made without departing from the spirit or scope thereof. It should be understood that the invention is intended to be limited only as defined in the appended claims.

What we claim is:

1. A process for the preparation of substituted 10-chloro-phenoxaphosphines and 10-bromo-phenoxaphosphines comprising reacting a substituted diphenyl ether with a phosphorus trihalide in the presence of at least one Lewis acid and reacting the resulting product with an amine to produce the substituted 10-halo-phenoxaphosphine.

2. The process of claim 1, wherein the reaction of the substituted diphenyl ether and a phosphorus trihalide is carried out at a temperature of 0 to 200° C.

3. The process of claim 2 wherein the temperature is 0 to 150° C.

4. The process of claim 2 wherein the temperature is 50 to 120° C.

5. The process of claim 1 wherein the reaction of the substituted diphenyl ether and phosphorus trihalide is carried out at a pressure of 0.1 to 2 MPa.

6. The process of claim 1 wherein the phosphorus trihalide is used in at least stoichiometric equivalents of the diphenyl ether.

7. The process of claim 6 wherein the Lewis acid is used in stoichiometric excess of the substituted diphenyl ether.

8. The process of claim 7 wherein the stoichiometric excess is 1.2 fold.

9. The process of claim 1 wherein phosphorus trichloride is the phosphorus halide.

10. The process of claim 1 wherein the reaction of the substituted diphenyl ether and phosphorus trihalide is carried out in the presence of a solvent.

11. The process of claim 1 wherein the amine is selected from the group consisting of trialkylamine of 3 to 12 carbon atoms, mixed tertiaryl alkylarylamine of 8 to 22 carbon atoms, alicyclic amine of 4 to 8 carbon atoms optionally with an oxygen heteroatom and a heterocyclic amine of 4 to 22 carbon atoms.

12. The process of claim 1 wherein the amine is triethylamine or pyridine.

13. The process of claim 1 wherein the molar ratio of amine to Lewis acid is 0.5:1 to 5:1.

14. The process of claim 13 wherein the molar ratio is 0.9:1 to 3:1.

15. The process of claim 13 wherein the molar ratio is 1:1 to 2.5:1.

16. The process of claim 1 wherein the amine addition is performed at −100° to 100° C.

17. The process of claim 16 wherein the temperature is −100° C. to 50° C.

18. The process of claim 16 wherein the temperature is −50° to 25° C.

* * * * *